United States Patent [19]

Takahashi et al.

[11] 4,227,887
[45] Oct. 14, 1980

[54] DETERMINATION OF TOTAL ORGANIC HALIDES IN WATER

[75] Inventors: Yoshihiro Takahashi, San Francisco; Robert T. Moore, Palo Alto; Robert J. Joyce, Cupertino, all of Calif.

[73] Assignee: Envirotech Corporation, Menlo Park, Calif.

[21] Appl. No.: 937,652

[22] Filed: Aug. 28, 1978

[51] Int. Cl.³ .............. G01N 31/12; G01N 31/16; G01N 33/18
[52] U.S. Cl. .................. 23/230 PC; 23/230 R; 204/1 T; 422/80
[58] Field of Search ............ 23/230 R, 230 PC; 422/78, 80; 204/1 T

[56] References Cited

U.S. PATENT DOCUMENTS

| | | | |
|---|---|---|---|
| 3,544,277 | 12/1970 | Lysyj et al. | 422/79 |
| 3,703,355 | 11/1972 | Takahasi et al. | 23/230 PC |
| 3,716,334 | 2/1973 | Pont | 23/230 PC |
| 3,853,474 | 12/1974 | Austin | 23/230 PC X |

OTHER PUBLICATIONS

Cedergrin, "A Modified Oxidative Microcoulometric Method for Determination of Sulfur in Hydrocarbons Containing Large Amounts of Chlorine", *Talanta*, vol. 24, Pergamon Press (1977 pp. 21-24.

R. C. Dressman, "An Evaluation of the Determination of Total Organic Chlorine (TOCl) in Water by Adsorption onto Ground Activated Carbon, Pyrohydrolysis, and Chloride-Ion Measurement", paper presented at Water Quality Technology Conference at Kansas City, Missouri, Dec. 5-6, 1977.

R. C. Dressman. "Procedure for the Application of the CAOX as Cl⁻ Method to Disinfected Water," addendum to R above), Water Supply Research Division, U.S. Environmental Protection Agency, Jun. 1, 1978.

D. H. Glaze et al., "Total Organic Halogen as Water Quality Parameter: Adsorption/Microcoulometric Method", Environmental Science & Technology, vol. 11, No. 7, Jul. 1977.

Kuhn et al., "Einige Untersuchungen zur Bestimmung von organischen Chlorverbindungen auf Aktivkohlen" (Several Investigations on Activated Charcoal for the Determination of Organic Chloro-Compounds), Vom Wasser, vol. 41 (1973), pp. 65-79, (English copy from the EPA.)

*Primary Examiner*—Arnold Turk
*Attorney, Agent, or Firm*—William S. Bernheim; John J. Morrissey

[57] ABSTRACT

A three phase process for determining total organic halides in water. The first phase is a sorptive process including passing a liquid through a packed bed of sorptive material thereby removing quantitatively, purgeable and non-purgeable, organic halides and thereafter passing an inorganic halide displacement wash solution through the bed to displace inorganic halides. The second and third phases are a combination combustion and titration whereby organic bromides and other organic halides entering the combustion phase are quantitatively titrated coulometrically. The second and third phases include in a first heating zone heating a sample, such as the sorptive material following the first phase, in the presence of a mild oxidant to a temperature sufficient to vaporize water; in a second heating zone heating any remaining sample from the first heating zone and gases therefrom in the presence of an oxidant to a temperature sufficient to complete combustion of the sample and gases; and concurrently titrating coulometrically the gases from the second heating zone.

23 Claims, 2 Drawing Figures

DETERMINATION OF TOTAL ORGANIC HALIDES IN WATER

BACKGROUND OF THE INVENTION

1. Field of the Invention

This invention generally relates to determining the concentration of organic halides in samples, such as drinking water and wastewater.

2. State of the Art

A number of methods have been proposed for measuring total organic halides (essentially organically bound chloride, bromide and iodide species) in drinking water and wastewater. These methods have various deficiencies including an inability to quantitatively remove organic halide species, both purgeable and nonpurgeable, from drinking water or wastewater and an inability to quantitatively titrate bromide species coulometrically. Other deficiencies include slowness and poor reproducibility.

OBJECTS OF THE INVENTION

It is an object of the present invention to provide a process and apparatus for removing purgeable and nonpurgeable organic halides quantitatively from drinking water and wastewater.

Another object of the invention is to provide a combustion and titration apparatus and process for measuring organic bromides quantitatively.

Other objects include faster and more reproducible results.

A BRIEF DESCRIPTION OF THE DRAWINGS

Further objects and advantages of the invention may be readily ascertained by reference to the following description and appended drawings, which are offered by way of description only and not in limitation of the invention, the scope of which is defined in the appended claims.

In the drawings:

FIG. 1 is a schematic of an apparatus for accomplishing a sorption according to the invention; and FIG. 2 is a schematic of an apparatus for accomplishing a combustion and titration according to the invention.

DETAILED DESCRIPTION OF A PREFERRED EMBODIMENT OF THE INVENTION

The invention generally relates to an apparatus and process for determining total organic halides (primarily organically bound chlorides, bromides and iodides) in drinking water or wastewater. The process includes three phases: (1) a sorption in which a liquid sample is passed through a bed of sorptive material to remove by adsorption and absorption the organic compounds in the sample; (2) a combustion in which the sorptive material inclusive of the removed organic compounds is oxidized to convert any organic halides presence (except fluorides) to titratable halides; and (3) a titration in which the titratable halides are coulometrically measured in a conventional acidic-silver titration cell. The first phase and second two phases are separable processes which are useful for achieving their separate purposes and also complement one another in achieving a quantitative determination of the total organic halide concentration in drinking water or wastewater.

Figure 1:
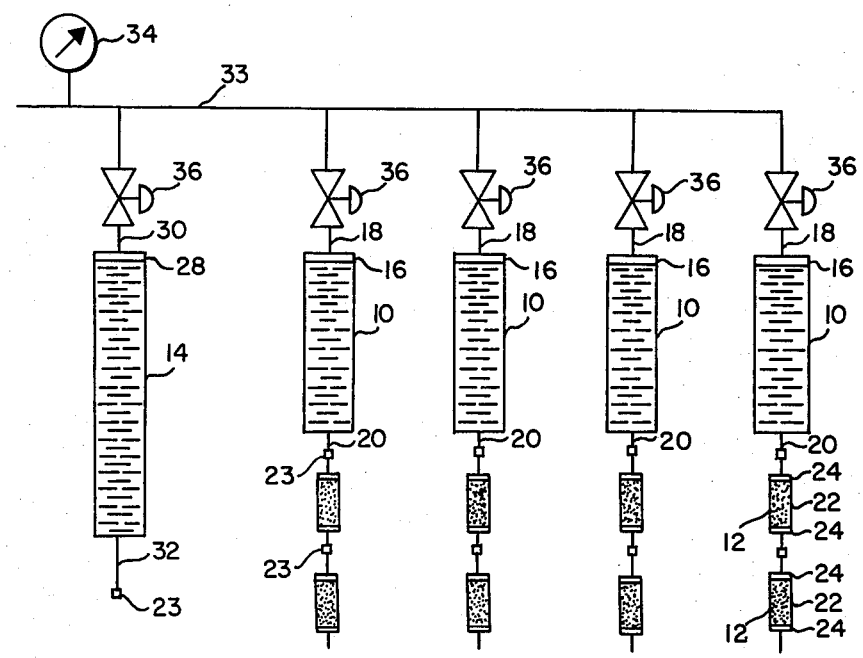

A suitable apparatus for the sorption is schematically shown in FIG. 1. The apparatus basically includes a plurality of containers 10, into which liquid samples are placed, mounted on a frame (not shown); a plurality of columns 12, in which a bed 22 of sorptive material can be formed, detachably mounted in series (typically in pairs) to the containers 10 to receive flow from the containers 10; a nitrate ion wash reservoir 14 mounted to the frame and to which the columns 12 can be detachably mounted to receive wash solution from the reservoir 14; and means for delivering at a measured rate an inert gas to the containers 10 and reservoir 14.

In more detail, the containers 10 provide means for receiving a liquid sample with a minimum of agitation, holding the sample in a quiescent state, and releasing the sample at a measured rate. The containers 10 can consist of glass cylinders, each having a removable gas-sealable cap 16 for filling the containers 10 and a capacity to hold approximately 100 ml of sample. Further, each of the containers 10 includes an inlet 18 for admitting an inert gas through the cap 16 and an outlet 20 for discharging the liquid sample at a rate proportional to the rate at which the inert gas is admitted at the inlet 18. The outlet 20 and the columns 12 can be interconnected by, for example, a threaded O-ring compression fitting 23.

The columns 12 provide means for forming and retaining a bed 22 of sorptive material so that a liquid sample can be passed through the material with good liquid-material contact so as to accomplish adequate removal from the sample of organics including organic halides. The columns 12 can consist of a length of standard 2 mm I.D. capillary tubing into which the sorptive material is packed to form a bed 22 and held in position with quartz wool 24. The columns 12 can be connected to one another with suitable compression fitting 23.

The reservoir 14 provides means for holding a wash solution to be passed through the sorptive material following the liquid sample to displace inorganic halides adsorbed or absorbed by the material. The reservoir 14 can be a glass container having a removable gas-sealable cap 28 to allow filling of the container and a capacity of approximately 100 ml. Further, the reservoir 14 includes an inlet 30 for admitting an inert gas through the cap 28 and an outlet 32 for discharging the wash solution at a rate proportional to the rate at which the inert gas is admitted at the inlet 30. The outlet 32 can be fluid-sealably connected to the columns 12 with a suitable compression fitting 23.

The means for delivering an inert gas at a measured rate can be provided by a pressurized tank (not shown) and associated gas lines 33, gauges 34 and valves 36.

In those cases in which the liquid sample has been chlorinated, additional means is provided for mixing a reducing agent, for example, sodium sulfite or sodium thiosulfate, with the liquid sample prior to passing the sample through the sorptive material. The presence of the reducing agent eliminates residual chlorine interference.

Figure 2:
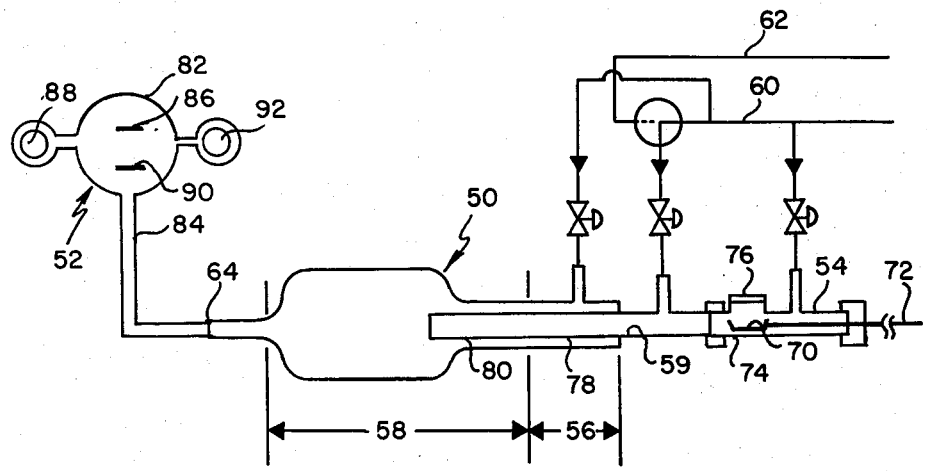

A suitable apparatus for the combustion and titration is schematically shown in FIG. 2. A suitable commercial apparatus for the process is the MCTS-20 microcoulometric titration system, available from the Dohrmann Division, Envirotech Corporation, Santa Clara, Calif. 95050.

The apparatus generally includes a furnace unit 50 and a titration unit 52 which is in gas flow communication with the furnace unit 50 to receive gases therefrom. The furnace unit 50 basically includes a sample receiver 54, a first heating zone 56 connected to the sample receiver 54, a second heating zone 58 connected to the first heating zone 56 and an inlet conduit 59 extending from the receiver 54 through the first heating zone 56 to the second heating zone 58. Further, the furnace unit 50 includes a first gas source 60 for introducing a gas to the sample receiver 54 to flow through the furnace unit 50 to the titration unit 52; a second gas source 62 for introducing during certain periods a second gas to the second heating zone to flow through to the titration unit 52; and an outlet conduit 64 for conveying gaseous output from the furnace unit 50 to the titration unit 52.

In more detail, the sample receiver 54 of the furnace unit 50 provides means for receiving a sample into the furnace unit 50 and gas sealing it therein. The combustion and titration phase of the overall process is not limited by the physical state of the sample; different conventional sample receivers are available for receiving solids, liquids or gases. In this process, a sample receiver 54 for receiving wet solids, i.e. sorptive material from the sorption phase, is utilized. The sample receiver 54 includes a quartz boat 70 movable along conduit 59 manually or automatically by means of a push rod 72 between three positions: a first position 74 is below a sealable opening 76 through which the sorptive material is introduced to the boat 70, a second position 78 is in the first heating zone 56, and a third position 80 is in the second heating zone 58.

The first heating zone 56 provides means for heating the material in the boat 70 to evaporate water and readily volatile organics associated with the material at a rate of heating insufficient to cause sputtering of water or sample material. For better temperature control in the heating zone 56, the conduit about the first position 74 can be surrounded with cooling coils and/or heating elements.

The gases generated in the first heating zone 56 are carried by gas introduced by the first gas source 60 to the titration unit 52 via the second heating zone 58.

The second heating zone 58 provides means for heating the remaining material in the boat 70 to complete combustion of the remaining organics (including sorptive material) to leave an ash residue. The gases generated in the first heating zone 56 are also combusted in the second heating zone 58. The second heating zone 58 can be a chamber which can be heated to a sufficiently high temperature and to which a source of oxidant can be introduced, i.e. gas introduced by either or both the first gas source 60 and the second gas source 62.

The conduit 64 connecting the furnace unit 50 with the titration unit 52 provides means for transferring the gases coming off the material in both heating zones to the titration unit 52. The conduit 64 can be simple glass tubing, normally, surrounded by a heating strip to maintain the temperature of the tubing above 100° C. to avoid condensation of water in the tubing.

A suitable titration unit 52 is described in U.S. Pat. No. 3,427,238 and that description is incorporated by reference. As shown in FIG. 2, the unit 52 basically includes an electrolytic cell 82 for containing an electrolyte; an inlet 84 for admitting the gaseous products from the furnace unit 50; and an anode electrode 86, a cathode electrode 88 and a sensor electrode 90 each disposed in the electrolyte. The titration unit 52 also includes a reference electrode 92 disposed in electrolytic communication with the contained electrolyte, suitable electrical circuitry (not shown) for operation of the unit 52, and a strip chart or other measuring device (not shown) for recording the use of power which is proportional to the halides precipitated in the cell 82.

The process begins with the sorption phase which includes basically the steps of passing a known quantity of a liquid sample containing, purgeable and non-purgeable, organic halides through a packed bed 22 of sorptive material to adsorb and absorb the organic halides onto the material, and thereafter passing a halide ion displacement wash solution through the bed 22 to displace inorganic halides from the material.

In more detail, approximately 100 ml of a liquid sample, such as drinking water or wastewater, containing up to 500 ppb organic halide (for a sample having higher organic halides, a proportionally reduced sample volume can be processed or dilution can be used to lower the organic halide concentration) is placed into one of the containers 10 with a minimum of agitation to minimize escape of purgeable organics. A single container 10 is sufficient; the additional containers 10 are provided so that confirmation measurements or measurements on other samples can be made concurrently.

The container 10 containing the sample is gas-sealed with cap 16 and a gas line 33 is connected to the inlet 18. First and second columns 12, arranged in series and each inclusive of a bed of sorptive material, are connected to the outlet 20. The sorptive material is preferably, because of the later combustion of the material, a tightly packed bed of finely ground activated carbon in the range of about 100–400 mesh. Alternatively, synthetic porous polymer beads can be used, especially if the purpose for which the organics are removed, such as for other analysis techniques including liquid chromatography, does not include a combustion of the sorptive material. For a 100 ml sample, 40 mg of activated carbon in each column 12 is suitable. Under these conditions all of the organic halides should be removed in the column 12 nearest the container 10. The second column provides, as described infra, confirmation of the sorption efficiency of the first column. Confirmation is provided by comparing the background reading of the halide content of the sorptive material, determined separately with the reading for the second column.

An inert gas is introduced to the container 10 through the line 33 at a rate so that the sample flows through the columns 12 at a rate of approximately 3 ml/min. This flow rate is preferred because it allows sufficient diffusion in the columns 12 to accomplish the sorption. The passage of a measured quantity of about 100 ml through the columns 12 takes about 30 minutes. The gas, such as helium or argon, introduced to the container 10 should be non-reactive with the sample.

After a measured quantity of sample has passed through the columns 12, the columns are detached from the container 10 and attached to reservoir 14. The reservoir 14 contains a halide ion displacement wash solution which is passed through the beds in the same manner as the liquid sample was, by introducing an inert gas to the reservoir so that the solution flows through the columns 12 at a rate of approximately 1 ml/min. The solution displaces inorganic halides such as sodium chloride from the sorptive material. The quantity of solution passed through the columns 12 need not be measured precisely and approximately 2 ml is sufficient. A suitable solution is an aqueous solution having a nitrate ion ($NO_3^-$) concentration of about 0.01 N and a pH of about 2. If not removed, the inorganic halides typically found in drinking water would mask the organic halides to a degree that the results would be meaningless.

Following the solution wash, the sorptive material is ready for the combustion and titration phases. It has been found that the above sorption process achieves good recovery of purgeable organic halides, such as $CHCl_3$, and non-purgeable organic halides, such as 2,4,6 tribromophenol. It is believed that these results are achieved because the sample is not agitated during the process steps of the sorption.

The combustion and titration basically include an oxidation, which is carried out in the furnace unit 50, and a titration, which is carried out in titration unit 52. The oxidation includes basically the steps of in the first heating zone 56 heating a gas, liquid or solid sample in the presence of a mild oxidant but in the absence of oxygen to a temperature sufficient to vaporize water from the sample but at a rate of heating insufficient to cause water sputtering; and thereafter in the second heating zone 58 heating any remaining sample and any gases generated in the first heating zone 56 in the presence of an oxidant to a temperature sufficient to complete combustion of the sample and generated gases, thereby to convert any organic halides present in the sample to titratable halides while minimizing the production of bromine and oxybromo acids, e.g. hypobromous acid.

In more detail, the oxidation begins with the sample, in this case the wet sorptive material from the first column 12 nearer the container 10, being introduced to the furnace unit 50. The introduction is through opening 76 into the boat 70 which is in its first position 74. The boat 70 is then advanced along conduit 59 to introduce the sample into the first heating zone 56.

A minimum temperature in the first heating zone 56 to vaporize water associated with the sample is about 60° C. A maximum temperature to avoid sputtering is about 400° C. A preferred range is between about 100° C. and 300° C. and most preferred is a temperature of about 200° C.

The heating is in the presence of a mild oxidizing agent. This is accomplished by having the first gas source 60 introduce a gas containing a mild oxidizing agent. Pure $CO_2$ is preferred as the gas.

Alternatively, otherwise inert gases containing from 10% to 20% or more $CO_2$ are suitable. Pure $NO_2$ is also suitable, as are otherwise inert gases containing 10% or more $NO_2$. A limitation is put on the presence of $O_2$ at less than about 10% and preferably zero. The presence of oxygen at this point encourages the generation of bromine gas and oxybromo acids both of which are not coulometrically titratable species and, hence, not measured in the titration cell.

A residence time of thirty seconds for liquid or solid samples in the first heating zone is minimal and a residence time of about one minute is preferred.

From the first heating zone 56, the boat 70 is advanced along the conduit 59 to introduce the remaining sample into the second heating zone 58. Gases generated from the sample in the first heating zone 56 are also introduced by being carried by the gas from the first gas source 60.

In detail, in the second heating zone 58, any remaining sample and the generated gases are first heated to a temperature sufficient to initiate combustion of the sample preferably initially in the presence of a mild oxidant, such as described previously. To complete combustion, an oxygen containing gas is introduced to the second heating zone 58. An oxygen containing gas can be present initially rather than a mild oxidant, although not preferred.

The oxygen containing gas is preferably introduced by a combination of gases from the first gas source 60 and the second gas source 62. Preferably the oxygen concentration of this introduced gas is between about 20% and 70%. With an oxygen concentration below 20% the oxidation takes unreasonably long, above about 70% the oxidation of the activated carbon does not dominate sufficiently to prevent unreasonable production of bromine gas and oxybromo acids.

A minimum temperature in the second heating zone 58 to initiate combustion is about 500° C. A maximum temperature because of apparatus limitations, such as the softening temperature of the quartz boat 70, is about 1200° C. A preferred range is between about 700° C. and 1000° C. Most preferred is a temperature of about 800° C.

A residence time for generated gases introduced to the second heating zone 58 of at least about 15 seconds is preferred. A residence time for remaining liquid and solid sample of at least about two minutes is preferred. Applicants have found it convenient to introduce 200 cc/min of gas to the furnace unit 50 at all times. Of this 200 cc/min, 100 cc/min is always pure $CO_2$ (first gas source 60), and the other 100 cc/min is pure $CO_2$ (first gas source 60) except during the later part of the combustion in the second heating zone 58 when 100 cc/min of pure $O_2$ (note the $O_2$ concentration of total flow is 50%) is introduced to the second heating zone (second gas source 62).

The gases in the furnace unit 50 are continuously carried to the titration unit 52 where, in a conventional manner described in U.S. Pat. No. 3,427,238, the halides in the gases are titrated coulometrically.

The gases from the furnace unit 50 are carried into the cell 82 through inlet 84. As the halides go into solution, chloride, bromide and iodide ions are generated and react very rapidly with silver ions in the electrolyte to form precipitates of silver chloride, silver bromide and silver iodide respectively. This reduces the concentration of the silver ions and changes the tendency of silver to come off the sensing electrode 90. This changes the potential on the sensing electrode 90, and as a result the circuitry causes the anode 38 to become more positive. This causes more electrons to be pulled out of the anode 38, which allows more silver ions to escape into the electrolyte to restore the silver ion concentration.

Similarly, the sorptive material of the second column 12 is processed through the combustion and titration phases. Preferably, the material in the second column 12 will contain no additional organic halides, the organic halides having been removed in the first column 12. As a consequence, the halide reading for this second material should be approximately equal to the background reading of the halide content of the sorptive material. The chlorine background of the activated carbon is normally constant for all carbon from the same batch and, thus, this background can be determined independently. A total organic halide determination for the first column is, hence, derived by subtracting the background reading from the reading for the material in the first column 12.

The detection is limited to approximately 1 microgram/liter of original liquid sample processed in the sorption phase. The reproducibility is the higher of about ±1 microgram/liter or ±3% of the total organic halide.

It is to be appreciated that the sorptive phase of the process is useful with other techniques for measuring the organic halides, such as liquid chromatography or solvent extraction. Likewise, the combustion and titration phases are not limited to samples prepared by the above sorption. The samples can be in liquid, solid or gas form. Further use of this technique is advantageous whenever a sample contains bromide components which would otherwise pass through a titration as unmeasurable bromine gas or oxybromo acid.

We claim:

1. A process for converting organic halides in a gas, liquid or solid sample, derived from drinking water or wastewater, to coulometrically titratable halides comprising the steps of:
   a. in a first heating zone, heating a sample in the presence of a mild oxidant but absence of oxygen to a temperature sufficient to vaporize water from the sample but at a rate of heating insufficient to cause water sputtering; and
   b. in a second heating zone, heating any remaining sample and any gases generated in the first heating zone in the presence of an oxidant to a temperature sufficient to complete combustion of the sample and generated gases, thereby to convert any organic halides present to coulometrically titratable halides.

2. A process according to claim 1 wherein the heating in the first zone is to a temperature between about 60° C. and 400° C.

3. A process according to claim 1 wherein the heating in the first zone is to a temperature of about 200° C.

4. A process according to claim 1 wherein the mild oxidizing agent is a gas stream having a carbon dioxide concentration of at least about 20%.

5. A process according to claim 1 wherein the temperature in the second heating zone is between about 500° C. and 1200° C.

6. A process according to claim 1 wherein the heating in the second zone is to a temperature of about 800° C.

7. A process according to claim 1 wherein initially the heating in the second heating zone is in the presence of a mild oxidizing agent and in the absence of oxygen.

8. A process according to claim 7 wherein after said initial heating in the second heating zone an oxygen containing gas is introduced.

9. A process according to claim 8 wherein the oxygen concentration ofthe gases introduced to the second heating zone is between about 20% and 70%.

10. A process according to claim 1 further including steps to derive the sample from drinking water or wastewater, the steps comprising:
    a. passing a quantity of a liquid containing organic halides through a packed bed of sorptive material to adsorb and absorb the organic halides onto the material thereby to remove quantitatively, purgeable and non-purgeable, organic halides from the liquid; and
    b. then passing a halide ion displacement wash solution through the bed to displace inorganic halides from the material thereby to yield a suitable sample, the sorptive material inclusive of the adsorbed and absorbed organic halides.

11. A process according to claim 1 further including a step to titrate the halides generated in the process, the step comprising: coulometrically titrating the gaseous output from the second heating zone in an acidic-silver titration cell thereby to measure the halides in the gaseous output.

12. A process for removing purgeable and non-purgeable organic halides from a liquid such as drinking water or wastewater, and for quantitatively determining the concentration of said organic halides in said liquid, said process comprising the steps of:
    a. passing a known quantity of liquid containing organic halides through a packed bed of sorptive material at a flow rate allowing diffusion so that the organic halides are adsorbed and absorbed onto the sorptive material;
    b. thereafter passing a halide ion displacement wash solution through the bed to displace inorganic halides from the sorptive material; and
    c. converting the organic halides adsorbed and absorbed by the sorptive material to coulometrically titratable halides, thereby enabling determination of the concentration of organic halides in the liquid, the conversion of said organic halides to coulometrically titratable halides being accomplished by an initial heating of said sorptive material with said organic halides adsorbed and absorbed thereon in the presence of a mild oxidant but absence of oxygen to a temperature sufficient to vaporize water therefrom but at a rate of heating insufficient to cause water sputtering, followed by a further heating of said sorptive material with said organic halides adsorbed and absorbed thereon, and of any gases generated by said initial heating, in the presence of an oxidant to a temperature sufficient to cause complete combustion of said sorptive material and generated gases, thereby converting any organic halides present to titratable halides.

13. A method for converting organic halides in a sample to coulometrically titratable halides, said sample having been pretreated to remove inorganic halides therefrom, said method comprising the steps of:
    (a) heating said sample at a relatively low first temperature to vaporize water and low-temperature volatile organics from said sample, thereby leaving a low-temperature residue; said heating at said first temperature occurring at a rate that substantially precludes sputtering of said sample, said water and said low-temperature residue; said heating at said first temperature occurring in the presence of a mild oxidant but in the absence of oxygen;
    (b) oxidizing said low-temperature volatile organics at a second temperature, said second temperature being higher than said first temperature, in the presence of an oxidant, whereby any organic halides present in said low-temperature volatile organics are converted to coulometrically titratable halides; and
    (c) oxidizing said low-temperature residue at said second temperature in the presence of an oxidant until complete combustion of said low-temperature residue occurs, whereby any organic halides present in said low-temperature residue are converted to coulometrically titratable halides.

14. The method of claim 13 wherein said first temperature is in the range from 60° C. to 400° C.

15. The method of claim 14 wherein said first temperature is 200° C.

16. The method of claim 13 wherein said mild oxidant is carbon dioxide.

17. The method of claim 16 wherein said heating of said sample at said first temperature occurs in a first zone through which a stream of gas containing carbon dioxide is caused to pass.

18. The method of claim 13 wherein said second temperature is in the range from 500° C. to 1200° C.

19. The method of claim 18 wherein said second temperature is 800° C.

20. The method of claim 13 wherein said oxidizing of said low-temperature volatile organics and said low-temperature residue at said second temperature occurs for an initial period of time in the presence of a mild oxidant but in the absence of oxygen.

21. The method of claim 20 wherein, after said initial period of time has elapsed, said oxidizing of said low-temperature volatile organics and said low-temperature residue occurs in the presence of an oxygen-containing gas.

22. The method of claim 20 wherein said oxidizing of said low-temperature volatile organics and said low-temperature residue at said second temperature occurs in a second zone through which a stream of gas containing said mild oxidant is caused to pass.

23. A process for converting organic halides in a water-containing sample to measurable halides, said process comprising the steps of:
(a) in a first heating zone, heating said sample in the presence of a mild oxidant but in the absence of oxygen, said heating in said first heating zone causing water to vaporize from said sample but not causing water to sputter; and thereafter
(b) in a second heating zone, heating the remaining sample and any gases generated in the first heating zone in the presence of an oxidant, said heating in said second heating zone causing complete combustion of the sample and generated gases, thereby converting any organic halides present to measurable halides.

* * * * *